(12) United States Patent
Forsell (10) Patent No.: US 9,610,455 B2
(45) Date of Patent: Apr. 4, 2017

(54) MEDICAL SYSTEM COMPRISING IMPLANTS

(76) Inventor: Peter Forsell, Bouveret (SE)

(*) Notice: Subject to any disclaimer, the term of this patent is extended or adjusted under 35 U.S.C. 154(b) by 804 days.

(21) Appl. No.: 13/384,387

(22) PCT Filed: Jul. 19, 2010

(86) PCT No.: PCT/SE2010/050859
§ 371 (c)(1),
(2), (4) Date: Jan. 17, 2012

(87) PCT Pub. No.: WO2011/008165
PCT Pub. Date: Jan. 20, 2011

(65) Prior Publication Data
US 2012/0112556 A1    May 10, 2012

Related U.S. Application Data

(60) Provisional application No. 61/213,805, filed on Jul. 17, 2009.

(30) Foreign Application Priority Data

Jul. 17, 2009 (SE) ...................................... 0901002

(51) Int. Cl.
*H01F 27/42* (2006.01)
*H01F 37/00* (2006.01)
(Continued)

(52) U.S. Cl.
CPC ........ *A61N 1/3787* (2013.01); *A61N 1/37252* (2013.01); *H02J 5/005* (2013.01)

(58) Field of Classification Search
CPC .... A61N 1/37223; A61N 1/3787; H02J 5/005
(Continued)

(56) References Cited

U.S. PATENT DOCUMENTS 5,713,939 A * 2/1998 Nedungadi et al. ............ 607/33
5,735,887 A * 4/1998 Barreras et al. ................ 607/60
(Continued)

FOREIGN PATENT DOCUMENTS

EP        1235334       8/2002
JP        10117130      5/1998
(Continued)

OTHER PUBLICATIONS

U.S. Appl. No. 13/384,039 (Forsell) filed Jan. 13, 2012.
(Continued)

*Primary Examiner* — Dharti Patel (57) ABSTRACT

A medical system (100, 300) comprises internal parts (30, 32) for implantation in a patient and external parts (10, 12, 20). The external parts comprise an energy source (10) with a primary coil (12) and the internal parts comprise an electrically powered medical device (40, 41) and an energy receiver (30) with a secondary coil (32) for inductively receiving energy from the external energy source (10). The system (100, 300) is arranged to determine a balance between the energy received in the energy receiver (30) and the amount of energy used by the medical device (40, 41). The internal control unit (50) transmits feedback information to the external control unit (20), and the system (100, 300) is arranged to determine the feedback information based on a first (P1) and a second (P2) parameter.

22 Claims, 4 Drawing Sheets

(51) Int. Cl.
*H01F 38/00* (2006.01)
*A61N 1/378* (2006.01)
*A61N 1/372* (2006.01)
*H02J 5/00* (2016.01)

(58) Field of Classification Search
USPC .......................................... 607/61; 307/104
See application file for complete search history.

(56) References Cited

U.S. PATENT DOCUMENTS

| | | | |
|---|---|---|---|
| 5,876,425 A * | 3/1999 | Gord et al. ................. | 607/56 |
| 6,553,263 B1 * | 4/2003 | Meadows et al. ............. | 607/61 |
| 2004/0039423 A1 | 2/2004 | Dolgin | |
| 2009/0271047 A1 * | 10/2009 | Wakamatsu ............ | H02J 5/005 |
| | | | 700/295 |
| 2010/0211133 A1 | 8/2010 | Forsell | |
| 2010/0211134 A1 | 8/2010 | Forsell | |
| 2010/0217352 A1 | 8/2010 | Forsell | |
| 2010/0217353 A1 | 8/2010 | Forsell | |
| 2010/0222848 A1 | 9/2010 | Forsell | |
| 2010/0222849 A1 | 9/2010 | Forsell | |
| 2010/0234922 A1 | 9/2010 | Forsell | |
| 2011/0193688 A1 | 8/2011 | Forsell | |
| 2011/0196452 A1 | 8/2011 | Forsell | |
| 2011/0278948 A1 | 11/2011 | Forsell | |
| 2011/0301668 A1 | 12/2011 | Forsell | |
| 2012/0119700 A1 | 5/2012 | Forsell | |

FOREIGN PATENT DOCUMENTS

| | | |
|---|---|---|
| WO | WO2009/051533 A1 | 4/2009 |
| WO | WO 2009/051536 | 4/2009 |
| WO | WO 2009/070086 | 6/2009 |
| WO | WO2010/059096 A1 | 5/2010 |

OTHER PUBLICATIONS

U.S. Appl. No. 13/130,648 (Forsell) filed Aug. 3, 2011.
U.S. Appl. No. 13/130,634 (Forsell) filed Aug. 3, 2011.
U.S. Appl. No. 13/123,638 (Forsell) filed Apr. 11, 2011.
U.S. Appl. No. 13/123,168 (Forsell) filed Apr. 7, 2011.
U.S. Appl. No. 12/738,182 (Forsell) filed Apr. 15, 2010.
U.S. Appl. No. 12/682,835 (Forsell) filed Apr. 13, 2010.
U.S. Appl. No. 12/682,831 (Forsell) filed Apr. 13, 2010.
U.S. Appl. No. 12/682,477 (Forsell) filed Apr. 9, 2010.
U.S. Appl. No. 12/682,404 (Forsell) filed Apr. 9, 2010.
U.S. Appl. No. 12/682,336 (Forsell) filed Apr. 9, 2010.
U.S. Appl. No. 12/682,327 (Forsell) filed Apr. 9, 2010.
International Search Report for PCT/SE2010/050859, mailed Oct. 21, 2010.

* cited by examiner

MEDICAL SYSTEM COMPRISING IMPLANTS

This application is the U.S. national phase of International Application No. PCT/SE2010/050859 filed 19 Jul. 2010 which designated the U.S. and claims the benefit of U.S. Provisional No. 61/213,805, filed 17 Jul. 2009; and which claims priority to Swedish Application No.: 0901002-6 filed 17 Jul. 2009, the entire contents of each of which are hereby incorporated by reference.

TECHNICAL FIELD

The present invention discloses a medical system which comprises internal parts for implantation in a patient and external parts for use externally to the patient.

BACKGROUND

Medical systems which comprise implantable parts are well known. In many cases, the implantable parts consume energy and thus have to be supplied with energy, which can suitably be done from a power source which is external to the patient's body and which uses an external energy source. In order to facilitate the supply of energy as much as possible for the patient, an implanted device can be supplied with energy from an external energy source by means of inductive transfer of energy.

Inductive energy supply is a principle which works well for implanted systems, but systems known at present are not always able to adapt the amount of energy supplied to the implanted parts as rapidly as might be desirable in some situations.

SUMMARY

As stated above, there is a need for a solution by means of which energy can be supplied inductively to an implanted medical device from an external energy source, i.e. external to the patient's body, and by means of which the transfer of energy can be adjusted to the needs of the medical device in a manner which is more rapid than is possible by means of known such systems.

Such a solution is offered by the present invention in that it discloses a medical system which comprises internal parts for implantation in a patient and external parts for use externally to the patient.

The external parts comprise an energy source which is equipped with a primary coil for inductively transmitting energy to the implantable parts and a control unit for the control of the energy source. The internal parts comprise an electrically powered medical device, an energy receiver equipped with a secondary coil for inductively receiving energy for the medical device from the external energy source and a control unit for the control of the internal parts.

The inventive system is arranged to determine a balance between the amount of energy received in the energy receiver and the amount of energy used by the medical device, and the internal control unit is arranged to wirelessly transmit feedback information to the external control unit.

According to the invention, the system is arranged to determine the feedback information based on or relating to a first and a second parameter. The first parameter is based on the previously mentioned energy balance seen over a certain amount of time, and the second parameter is based on information determined by the system and relating to a coupling factor between the primary and the secondary coil.

The system of the invention is adapted to take into account at least both the first and second parameters in order to determine the amount of energy which should be transmitted by the external energy source, thus allowing for a rapid adjustment of said energy balance.

In one preferred embodiment the medical system comprises internal parts for implantation in a patient and external parts for use externally to the patient, the external parts comprising an energy source equipped with a primary coil for inductively transmitting energy to the implantable parts and an external control unit for the control of the energy source, the internal parts comprising an electrically powered medical device, an energy receiver equipped with a secondary coil for inductively receiving energy for the medical device from the external energy source and an internal control unit for the control of the internal parts, the system being arranged to determine a balance between the amount of energy received in the energy receiver and the amount of energy used by the medical device, in which system the internal control unit is arranged to wirelessly transmit feedback information to the external control unit, the system being characterized in that it is arranged to determine said feedback information based on or relating to a first and a second parameter and a third parameter, with the first parameter being based on said energy balance over a certain amount of time and the second parameter being based on information relating to a coupling factor between the primary and the secondary coils and the third parameter being based on at least one of;

a) in which the medical device also comprises a current regulator arranged to keep a current constant, the system being arranged to determine a difference between an input current to the current regulator and the current which the current regulator is arranged to keep constant, in which system said third parameter comprising or being based on said difference, b) in which the system also comprises a voltage regulator arranged to keep a voltage constant, the system being arranged to determine a difference between an input voltage to the voltage regulator and the voltage which the voltage regulator is arranged to keep constant, in which system said third parameter comprising or being based on said difference, and wherein the system being adapted to take into account at least both the first and second and third parameters to determine the amount of energy which should be transmitted by the energy source, thus allowing for a rapid adjustment of said energy balance.

It is important to understand the difference between the calibration of the system and the continuous regular feedback. The platform for the control of the energy transfer is the energy balance between the received and used energy by the implant (the used energy includes energy stored by the implant). However, to fast get an accurate level of energy transfer the transmission is initially calibrated with the coupling factor, basically the relation between the externally transmitted energy and the internally received energy. Furthermore, the coupling factor is followed over time to see if any new recalibration is needed, for example if the outer transmitting coil is moved in relation to the inner receiving coil. A rapid movement of the outer coil by for example an action by the patient could cause such a large change of the amount of received energy that the regular feed back normally taking small steps is not fast enough. Therefore a new calibration of the coupling factor could in one fast step recalibrate the energy transmission level. Furthermore, because the implant could not tolerate to get hot it is extremely important to use all energy very efficient. Normally the implant needs one or more fixed voltages or maybe also fixed current levels to work properly. When creating a fixed voltage level the voltage regulator needs a certain voltage span, that's to say a higher input voltage to the regulator than the fixed output voltage the regulator delivers. On the other hand if this difference between the input voltage and the fixed output voltage gets larger than needed the extra voltage will be consumed and still the regulator will deliver the requested output voltage although creating more heat. It is therefore of outmost importance to also keep track of any voltage or current difference over any regulator in the implanted implant to optimize energy consumption and heat production.

Additionally the system may also comprises a capacitor coupled in parallel over the medical device, the system being arranged to determine the total amount of energy stored in said capacitor, in which system the feedback information is also based on or comprises a parameter comprising or being based on the total amount of energy stored in the capacitor, the system also being adapted to take into this parameter in order to determine the amount of energy which should be transmitted by the external energy source.

In a further additional embodiment the system is adapted to use all at least all three parameters to determine the feedback information, wherein the feedback information comprises information comprising or relating to the amount of energy which should be transmitted by the external energy source.

Preferably the system is adapted to use the second and third parameters for determining the amount of energy which should be transmitted by the external energy source as a repeated calibration of the system, and to use the first parameter during operation of the system as a regular feed back in order to determine the amount of energy which should be transmitted by the external energy source during operation of the system.

In one embodiment of the system of the invention, the medical device also comprises a current regulator arranged to keep a current constant, and the system is arranged to determine a difference between an input current to the current regulator and the current which the current regulator is arranged to keep constant. In such a system, the feedback information is also based on or comprises a third parameter which comprises or is based on the current difference, and the system is adapted to also take into account the third parameter in order to determine the amount of energy which should transmitted by the external energy source.

In one embodiment of the system of the invention, the medical device also comprises a voltage regulator arranged to keep a voltage constant and the system is arranged to determine a difference between an input voltage to the voltage regulator and the voltage which the voltage regulator is arranged to keep constant. In such a system, the feedback information is also based on or comprises a third parameter which comprises or is based on the voltage difference, and the system is adapted to also take into account this third parameter in order to determine the amount of energy which should transmitted by the external energy source.

In one embodiment, the system is adapted to use all three parameters to determine the feedback information, and the feedback information comprises information comprising or relating to the amount of energy which should be transmitted by the external energy source.

In one embodiment, the system is adapted to use the second and third parameters for determining the amount of energy which should be transmitted by the external energy source, and to use the first parameter during operation of the system in order to determine the amount of energy which should be transmitted by the external energy source during operation of the system.

In yet one embodiment the system, the energy receiver comprises a first switch adapted to switch a connection between the secondary coil and the medical device on and off. The connection between the secondary coil and the medical device is switched on and off in order to achieve at least one of the following; a) enable the system to measure the coupling factor when the connection is off and b) using said switch as a security system, switching off when a security parameter determined by the internal control unit relating to the wireless energy transfer exceeds a certain threshold.

Suitably, the external control unit is adapted to transmit information wirelessly to the internal control unit which in turn is adapted to receive information wirelessly.

As will be realized, when it comes to determining the feedback parameters, this task can be divided between the internal and the external units (suitably their respective control units) in a rather large number of ways within the scope of the invention. In one embodiment, the external control unit can supply the internal control unit with information necessary to determine the second parameter, and the internal control unit can be given the task of determining all of the parameters as such, and to then supply them to the external control unit as feedback information. In such an embodiment, it is sufficient if the internal control unit supplies the external control unit with a percentage figure for a variation of the energy supply as the feedback information. Naturally, the percentage can be positive, negative or zero, in order to indicate an increase, a decrease, or a maintained energy transfer level.

In another embodiment, the internal control unit supplies the external control unit with information which is sufficient for the external control unit to establish the parameters which are used by the system, with that information then being the feedback information.

Again, as will be realized, the task of determining the feedback parameters can be divided in a large number of ways between the internal and external units within the scope of the invention, which will also impact on the nature and contents of the feedback information.

Thus, in one embodiment, at least one of the parameters is transmitted from the external control unit to the internal control unit, and the internal control unit determines the other parameters used by the system and transmits the feedback information to the external control unit as information on the amount of energy which should transmitted by the external energy source.

In one embodiment, information for determining at least one of the parameters is transmitted from the external control unit to the internal control unit, and the internal control unit determines the parameters used by the system and transmits the feedback information to the external control unit as information on the amount of energy which should transmitted by the external energy source.

In one embodiment, information for determining at least one of the parameters is transmitted as the feedback information from the internal control unit to the external control unit, and the external control unit determines the parameters used by the system as well as the amount of energy which should transmitted by the external energy source.

In one embodiment, at least one of the parameters is transmitted as the feedback information from the internal control unit to the external control unit, and the external control unit determines the other parameters used by the system as well as the amount of energy which should transmitted by the external energy source.

These and other embodiments and their advantages will become more evident from the following detailed description.

BRIEF DESCRIPTION OF THE DRAWINGS

The invention will be described in more detail in the following, with reference to the appended drawings, in which.

DETAILED DESCRIPTION

Figure 1:
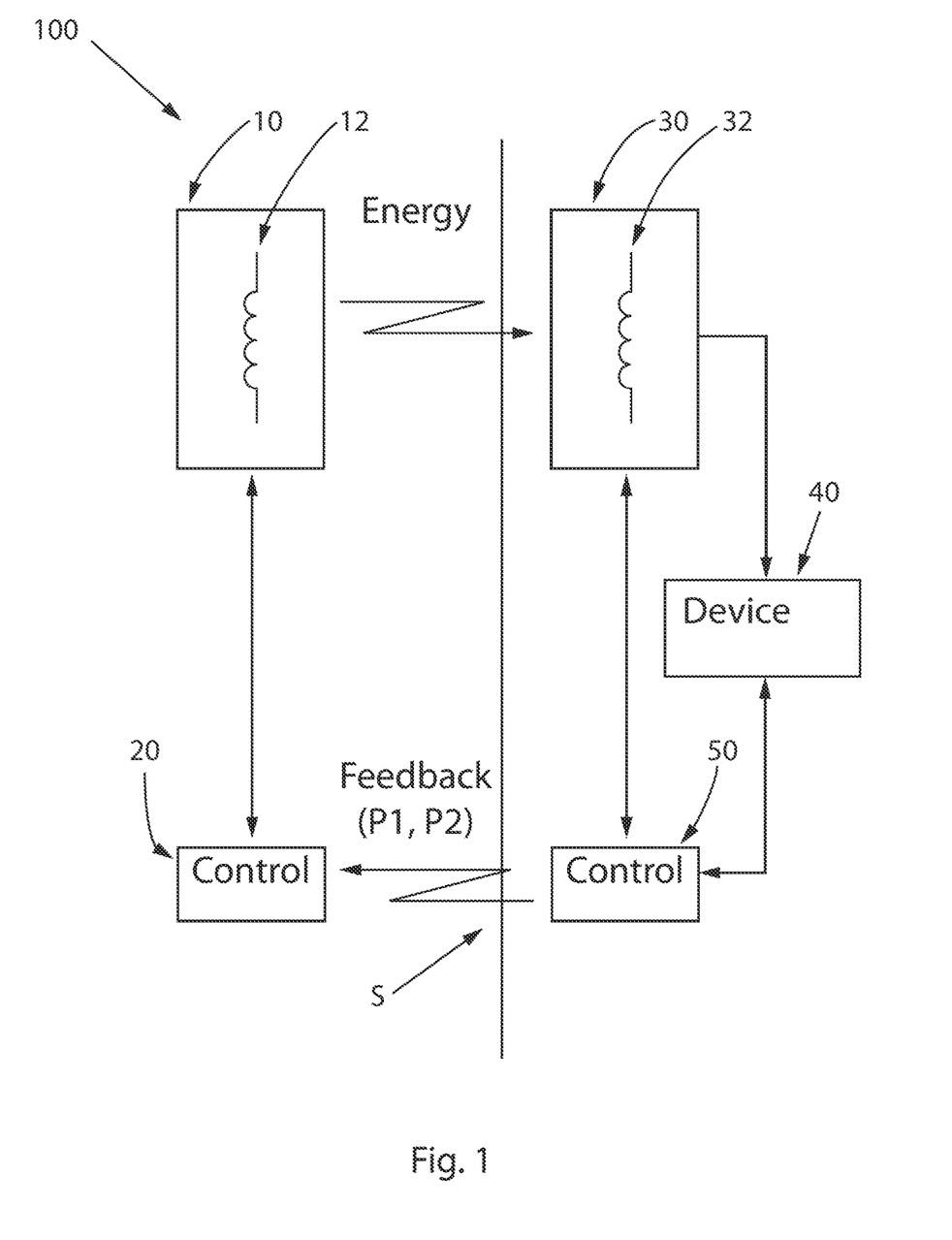
FIGS. 1-4 show schematic views of various embodiments of the invention.

FIG. 1 shows a schematic view of a first embodiment 100 of a medical system of the invention. As shown, the medical system 100 comprises parts intended for implantation in a patient as well as external parts intended to be used outside of the body of the patient in whom the internal parts are implanted. FIG. 1 shows the skin of a patient symbolically with a line "S", in order to show how the system is divided into external and internal parts. The external parts comprise an energy source 10 equipped with a primary coil 12 for transmitting energy wirelessly by means of induction to an internal energy receiver 30. Also comprised in the external parts is a control unit 20 for controlling, inter alia, the energy source 20 and its function.

The internal parts of the system 100 comprise a medical device 40, the energy receiver 30 and a control unit 50. The medical device 40 is electrically powered, and as indicated by the name, the purpose of the internal energy receiver 30 is to receive energy and to supply that energy to the medical device 40. The energy which the energy receiver 30 receives for the medical device is received wirelessly, by means of induction, for which reason the energy receiver is equipped with a secondary coil 32 for receiving such energy. A purpose of the internal control unit 50 is to control the internal parts.

As shown in FIG. 1, the internal control unit 50 is arranged to wirelessly transmit feedback information regarding, for example, the transfer of energy to the internal energy receiver 30, and as indicated in FIG. 1, the feedback information is based on or relates to a first and a second parameter, P1, P2.

Regarding the nature and function of the medical device 40, the invention is applicable to a large number of implantable medical devices, for which reason the medical device is only referred to by the generic term "medical device". However, examples of implantable electrically powered medical devices in which the present invention can be applied are devices which aid patients who suffer from urinary dysfunction, intestinal dysfunction, infertility, impotence, vascular and heart related diseases, reflux disease, obesity etc. The invention can also be used to assist patients with food passageway correlated devices, implanted drug delivery, drainage, etc.

A purpose of the present invention is to enable a more rapid adjustment of the energy which is transferred to the internal medical device 40, so that the energy which is transferred better corresponds to the needs of the medical device 40. To this end, the system 100 is arranged to determine the feedback information based on or relating to the first and second parameters P1, P2.

The system 100 is arranged to determine a balance between the amount of energy received in the energy receiver and the amount of energy used by the medical device, and to determine the first parameter P1 being based on this energy balance over a certain amount of time. The energy balance can either be specified as the balance between the total amount of energy received in the energy receiver and the amount of energy used by the medical device or as the balance between the rate of energy received in the energy receiver and the rate of energy used by the medical device. The amount of time over which the balance is determined is a design parameter which is adapted to the specific needs of each system and application, and may thus vary, but is suitably in the range of 50-200 ms, although the invention covers any range of time. In addition, the amount of time over which the balance is determined is suitably chosen to coincide with the feedback information, which is thus also suitably transmitted at intervals of 50-200 ms, or more often or more seldom.

The second parameter, P2, is based on information which relates to a coupling factor between the primary coil 12 and the secondary coil 32. The intervals of time at which this coupling factor is determined is a design parameter which is adapted to the specific needs of each system and application, and may thus vary. The coupling factor can also be used as a calibration parameter which is determined much more rarely than the energy balance or it may also be simultaneously controlled. However, the second parameter P2 will normally not change since it is related to the coupling factor, if the external coil is kept stationary.

The system 100 is adapted to take into account at least both the first P1 and the second P2 parameter in order to determine the amount of energy which should be transmitted by the external energy source 10, which will enable a rapid adjustment of said energy balance. The manner in which the system takes these parameters into account can vary, but a number of ways will be described below.

In one embodiment, the energy balance mentioned previously is determined by the internal control unit 50, suitably by means of a processor in cooperation with a memory in the control unit, by means of retrieving the data necessary for establishing the balance over the period of time in question. Thus, the processor checks the energy received by the energy receiver and the energy consumed by the medical device, and determines the balance.

In addition to this, in this example of an embodiment, the second parameter P2 is also determined by the internal control unit 50, suitably by the processor and the memory mentioned above. As mentioned, the second parameter P2 relates to the coupling factor between the primary coil 12 in the external energy source 10 and the secondary coil 32 in the internal energy receiver 30, suitably as seen over a certain interval of time. Suitably but not necessarily, the second parameter P2 is the coupling factor.

Thus, in such an embodiment, the internal control unit 50 needs information from the external control unit 20 in order to determine the coupling factor. This information is supplied to the internal control unit 50, suitably wirelessly, by the external control unit 20, and the internal control unit 20 then determines the coupling factor.

When the internal control unit has the coupling factor and the balance, it has both of the parameters P1 and P2, and can then determine the amount of energy which should be transmitted by the external energy source 10 in order to achieve an adjustment of the energy balance towards a desired figure. For example, if the desired figure for the balance is 98%, and the balance has been determined to be 85%, an increase is necessary. If the coupling factor has been determined to be ideal, i.e. 100%, the necessary increase is less than it would have been with a coupling factor of, for example, 50%.

Thus, taking the coupling factor and the balance into account, the internal control unit arrives at a conclusion regarding the "sign" of a change in the amount of energy which should be transmitted, so that an increase has a positive sign, "+", a decrease has a negative sign, "−", and a "steady state" is without sign. The change (if any) is then transmitted to the external control unit 10 as a combination of a sign and a number signifying a percentage, e.g. "+15", "−30", "0", etc, where they are interpreted and acted upon correspondingly by the external control unit 10. In this embodiment, the internal control unit 50 is thus arranged to transmit information wirelessly to the external control unit 10, suitably by means of radio transmission, although other means of wireless transmission can also be used within the scope of the present invention, such as, for example, ultrasound.

In further embodiments of the system of the invention, there is also a third parameter P3, which is used by the system.

Suitably, in those embodiments of the system in which there are three parameters, all three parameters are used by the system in order to determine the feedback information, and the feedback information comprises information comprising or relating to the amount of energy which should be transmitted by the external energy source.

In one embodiment of the invention, the system is adapted to use the second and third parameters for determining the amount of energy which should be transmitted by the external energy source, and to use the first parameter during operation of the system in order to determine the amount of energy which should be transmitted by the external energy source during operation of the system. Thus, the second and third parameters are used when initializing the system, for example when turning the system on, in conjunction with which the necessary energy level needs to be established, which may also need to be done at sparse intervals during operation of the system. However, in this embodiment, the first parameter is used to regulate the energy level, i.e. to see to it that the energy transmitted during operation of the system is on the level which has been established using the second and third parameters, so that the first parameter is used in order to "tune" the transmission of energy during operation of the system.

It is important to understand the difference between the calibration of the system and the continuous regular feedback. The platform for the control of the energy transfer is the energy balance between the received and used energy by the implant (the used energy is including by the implant stored energy). However, to fast get an accurate level of energy transfer the transmission is initially calibrated with the coupling factor, basically the relation between the externally transmitted energy and the internally received energy. Furthermore, the coupling factor is followed over time to see if any new recalibration is needed, for example if the outer transmitting coil is moved in relation to the inner receiving coil. A rapid movement of the outer coil by for example an action by the patient could cause such a large change of the amount of received energy that the regular feed back normally taking small steps is not fast enough. Therefore a new calibration of the coupling factor could in one fast step recalibrate the energy transmission level. Furthermore, because the implant could not tolerate to get hot it is extremely important to use all energy very efficient. Normally the implant needs one or more fixed voltages or maybe also fixed current levels to work properly. When creating a fixed voltage level the voltage regulator needs a certain voltage span, that's to say a higher input voltage to the regulator than the fixed output voltage the regulator delivers. On the other hand if this difference between the input voltage and the fixed output voltage get larger than needed the extra voltage will be consumed and still the regulator will deliver the requested output voltage although creating more heat. It is therefore of outmost importance to also keep track of any voltage or current difference over any regulator in the implanted implant to optimize energy consumption and heat production.

Figure 2:
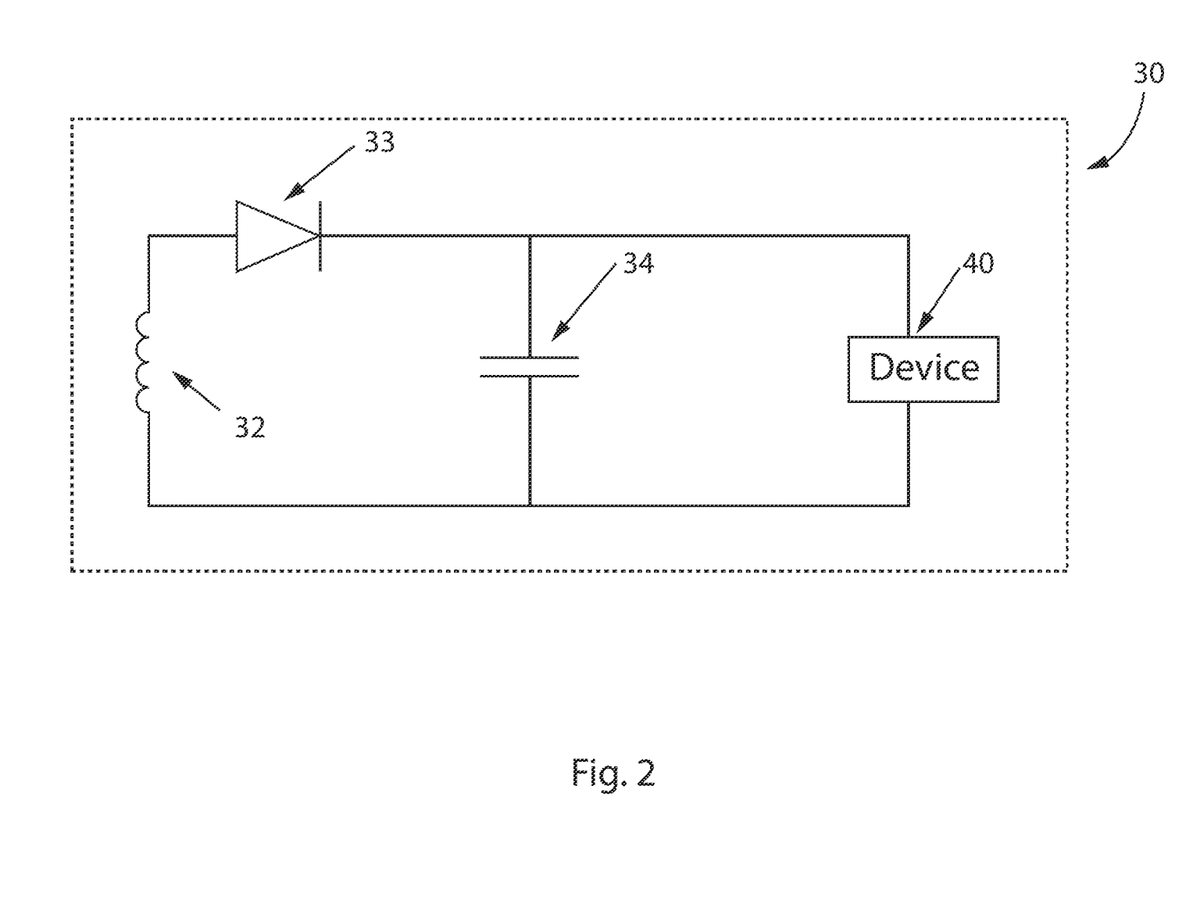

In one such "three parameter embodiment", which will be described with reference to FIG. 2, the system comprises a capacitor 34 coupled to the secondary coil 32. As shown in FIG. 2, the capacitor 34 is suitably arranged in the energy receiver 30, and is arranged in parallel with the secondary coil 32. Also, as shown in FIG. 2, in one embodiment the secondary coil is connected to the medical device 40 via a half wave rectifier, here shown as a diode 33, and the capacitor 34 is connected in parallel to the secondary coil 32 with the half wave rectifier between the capacitor and the secondary coil 32.

The capacitor 34 will, due to the design shown in FIG. 2, store energy when there is a voltage over the secondary coil 32, the amount of energy, "E", being defined by the expression $E=(V*Q)/2$, where V is the voltage over the capacitor and Q is the charge on each plate of the capacitor.

In the embodiment with the capacitor 34, the system of the invention is arranged to determine the total amount of energy, "E", stored in the capacitor 34, and the third parameter P3 comprises or is based on the total amount of energy, "E", stored in the capacitor, and the system is adapted to take into account the third parameter P3 in order to determine the amount of energy which should be transmitted by the external energy source. For example, if E is above a certain threshold value, this could be taken by the internal control unit 50 as an indication that the amount of energy to be transferred could be lowered or at least maintained at the same level, and if E is below the threshold value, this could be seen by the internal control unit 50 as an indication that the amount of energy to e transferred should be increased. Thus, it is suitably the internal control unit 50 that monitors the level of energy stored in the capacitor 34, and determines the third parameter P3.

Figure 3:
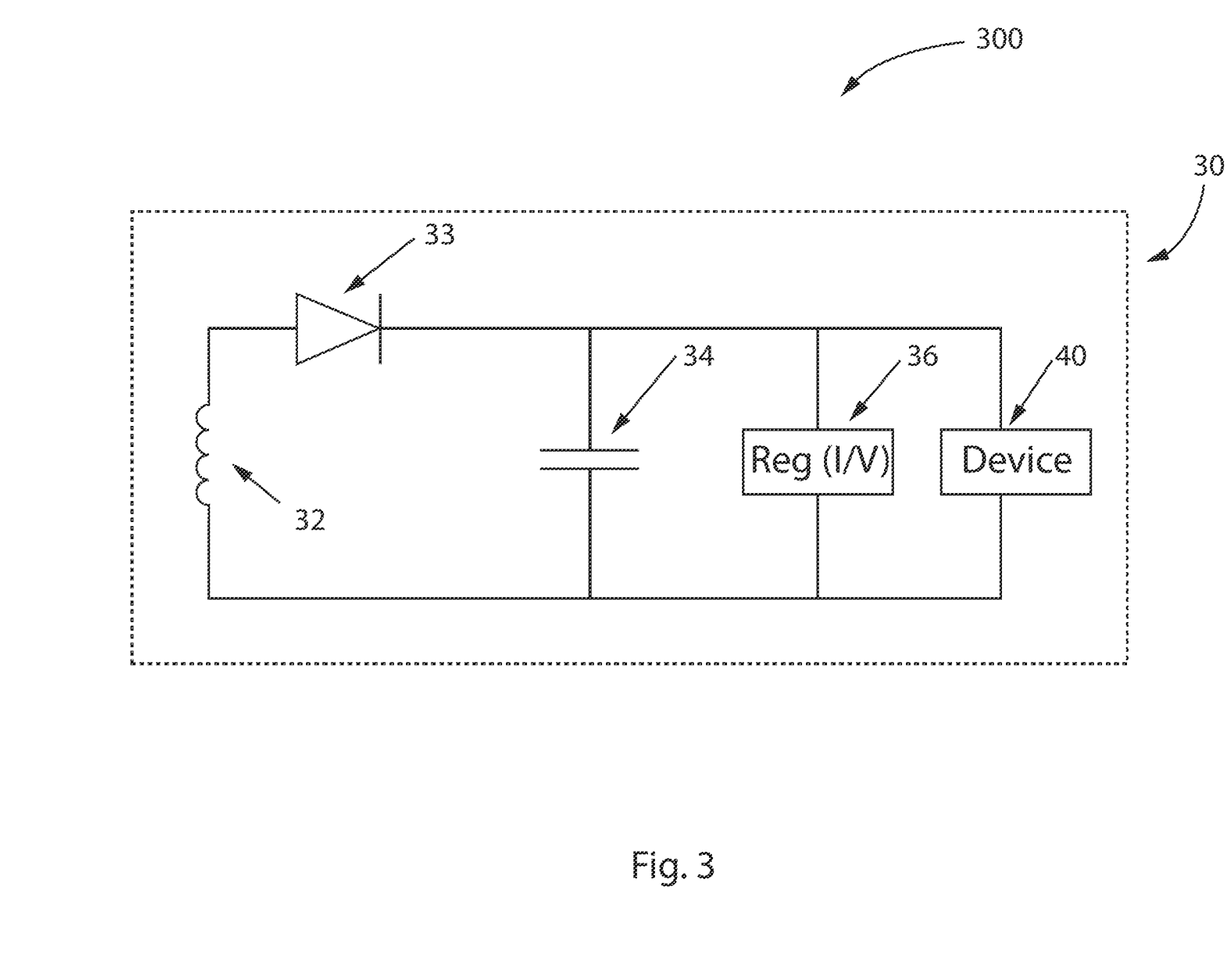

In a further "three parameter embodiment", schematically illustrated in FIG. 3, the medical device 40 also comprises a regulator 36, either a current regulator or a voltage regulator, which is thus arranged to keep a current or a voltage in the medical device constant. In such an embodiment, the system 300 is arranged to determine a difference between an input voltage/current to the voltage/current regulator and the voltage or current which the regulator is arranged to keep constant.

In this embodiment, the system bases the feedback information from the internal control unit to the external control unit on a third parameter P3 parameter which comprises or is based on this voltage/current difference. The system 300 is thus adapted to also take into account the "regulator" parameter P3 when determining the amount of energy which should be transmitted by the external energy source.

As shown in FIG. 3, the regulator 36 is in one embodiment a voltage regulator arranged to measure the voltage V over the medical device 40, as an alternative to which it can also be a current regulator arranged to measure the current I to the medical device 40.

In one embodiment, the system of the invention will further comprise an indicator in the external energy source, adapted to indicate a level of the coupling factor between the external coil 12 and the internal coil 32. In such an embodiment, the same or another indicator in the external energy source is suitably used for indicating an optimal placement of the primary coil in relation to the secondary coil in order to optimize the coupling factor.

Figure 4:
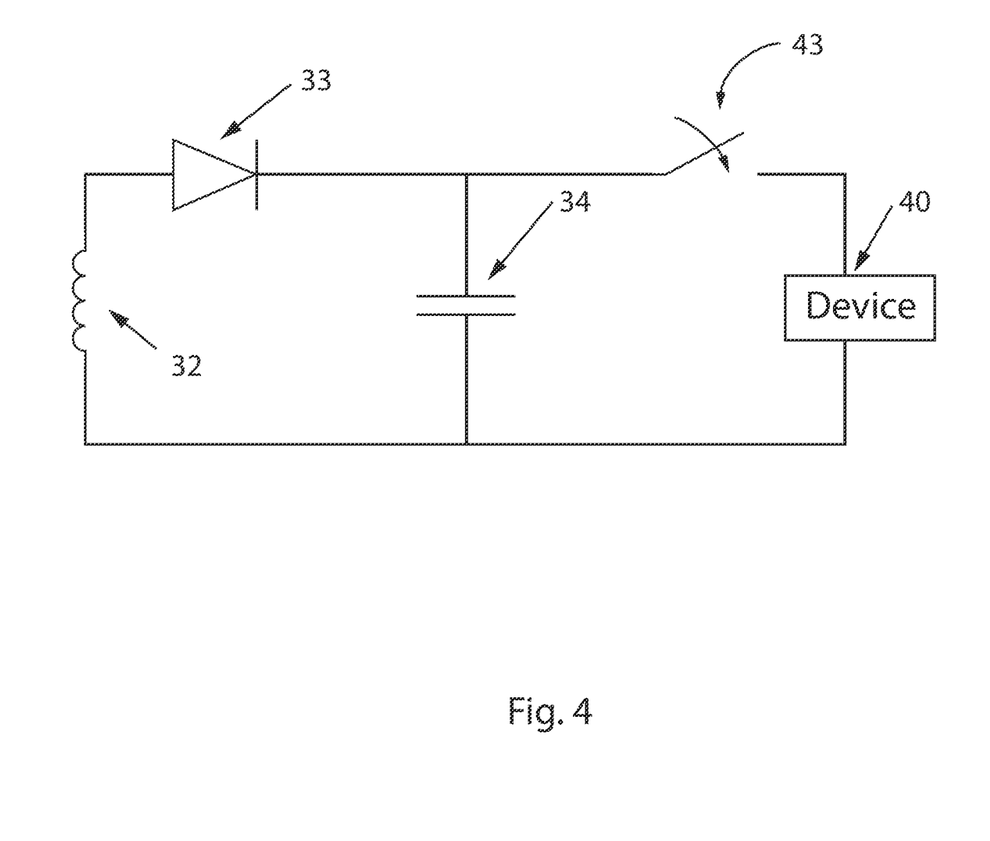

As shown in FIG. 4, in one embodiment of the system of the invention, the energy receiver comprises a first switch 43 which is adapted to switch a connection between the secondary coil 32 and the medical device 40 on and off, in order to enable the system to measure the coupling factor when the connection is off. Suitably, the internal control unit 50 handles the control of the switch 43.

The system 100, 300 may use the switch as a security system, switching off when a security parameter determined by the internal control unit relating to the wireless energy transfer exceeds a certain threshold.

In a further embodiment, the energy receiver 30 comprises an electronic component which is connected to the secondary coil for preventing the flow of electrical current between the secondary coil 32 and the medical device 40 during measurement of parameters, for example parameters related to related to the coupling factor. These measurements are suitably carried out by the control unit 50, and in one embodiment the electronic component is the diode 30 which has been described previously. Thus, measurements can be carried out either when the diode is biased by the voltage caused by the inductive voltage over the coil 32, or the control unit can cause the diode to be biased to block current to the medical device 40. If the diode 30 "blocks" the connection between the secondary coil 32 and the medical device 40, the secondary coil 32 will be substantially without an electrical load when the coupling factor is measured, which is beneficial for obtaining a good measurement result.

In one embodiment, the external energy source 20 comprises an electronic circuit (not shown) for comparing the feedback information with the amount of energy transmitted by the external energy source. Also, alternatively, this electronic circuit may be comprised in the control unit 20.

In a further embodiment, the system also comprises an internal control unit, preferably the control unit 50, which is adapted to determine the energy balance between the energy received by the energy receiver 30 and the energy used by the medical device 40; in this embodiment the system also comprises an external control unit such as the control unit 20 which is adapted to calibrate the transmission of wireless energy from the energy source 10 using feedback information.

In one embodiment, the system of the invention comprises at least one energy stabilizing unit in or connected to the medical device 40, arranged to stabilize received energy prior to use by the medical device 40.

The invention is not limited to the examples of embodiments described above and shown in the drawings, but may be freely varied within the scope of the appended claims.

The invention claimed is:

1. A medical system comprising internal parts for implantation in a patient and external parts for use externally to the patient, the external parts comprising an energy source equipped with a primary coil for inductively transmitting energy to implantable parts and an external control unit for the control of the energy source, the internal parts comprising an electrically powered medical device, an energy receiver equipped with a secondary coil for inductively receiving energy for the medical device from the external energy source and an internal control unit for the control of the internal parts, the internal control unit is arranged to wirelessly transmit feedback information to the external control unit, said feedback information comprising information based on or relating to a first, a second parameter and a third parameter, with the first parameter being based on an energy balance between the amount of energy received in the energy receiver and the amount of energy used by the medical device over a certain amount of time and the second parameter being based on information relating to a coupling factor between the primary and the secondary coils, wherein the coupling factor compares the transmitted amount of energy in the primary coil with the received amount of energy in the secondary coil, and the third parameter being based on at least one of;

a) in which the medical device also comprises a current regulator arranged to keep a current constant, the internal control unit being arranged to determine a difference between an input current to the current regulator and the current which the current regulator is arranged to keep constant, in which system said third parameter comprising or being based on said difference, b) in which the system also comprises a voltage regulator arranged to keep a voltage constant, the internal control unit being arranged to determine a difference between an input voltage to the voltage regulator and the voltage which the voltage regulator is arranged to keep constant, in which system said third parameter comprising or being based on said difference, and wherein the system being adapted to take into account at least both the first, second and third parameters to determine the amount of energy inductively transmitted from the primary coil to avoid heat generation within the internal parts due to excess energy.

2. A system according to claim 1, in which the system also comprises a capacitor coupled in parallel over the medical device, the internal control unit being arranged to determine the total amount of energy stored in said capacitor, in which system the feedback information is also based on or comprises a parameter comprising or being based on the total amount of energy stored in the capacitor, the system also being adapted to take into this parameter in order to determine the amount of energy which should be transmitted by the external energy source.

3. The system according to claim 2, in which a capacitor is coupled in parallel to the secondary coil via a half wave rectifier.

4. A system according to claim 1, which is adapted to use the second and third parameters for determining the amount of energy which should be transmitted by the external energy source as a repeated calibration of the system, and to use the first parameter during operation of the system as a regular feed back in order to determine the amount of energy which should be transmitted by the external energy source during operation of the system.

5. The system according to claim 1, in which the external control unit is adapted to transmit information wirelessly to the internal control unit, which in turn is adapted to receive information wirelessly.

6. The system according to claim 5, in which at least a part of at least one of said parameters or information for determining at least a part of at least one of said parameters is transmitted from the external control unit to the internal control unit, in which system the internal control unit determines at least one of said parameters used by the system and transmits the feedback information to the external control unit as information on the amount of energy which should transmitted by the external energy source.

7. The system according to claim 5, in which at least a part of at least one of said first, second or third parameters or information for determining at least a part of at least one of said parameters is transmitted from the external control unit to the internal control unit, in which system the internal control unit determines at least one of said parameters used by the system and transmits the feedback information to the external control unit as information about said parameters allowing the external control unit to determine the amount of energy which should be transmitted by the external energy source based on said parameters.

8. The system according to claim 1, in which at least a part of at least one of said parameters or information for determining at least a part of at least one of said parameters is transmitted as said feedback information from the internal control unit to the external control unit, and in which system the external control unit determines at least one of said parameters or part of parameters used by the system as well as the amount of energy which should transmitted by the external energy source.

9. The system according to claim 1, further comprising an indicator in the external energy source which is adapted to indicate a level of the coupling factor, and further for indicating an optimal placement of the primary coil in relation to the secondary coil.

10. The system according to claim 1, in which the energy receiver comprises a first switch adapted to switch a connection between the secondary coil and the medical device on and off.

11. The system of claim 10, wherein said connection between the secondary coil and the medical device is switched on and off in order to enable the system to measure the coupling factor when the connection is off and using said switch as a security system, switching off when a security parameter determined by the internal control unit relating to the wireless energy transfer exceeds a certain threshold.

12. The system of claim 10, wherein said connection between the secondary coil and the medical device is switched on and off in order to use said switch as a security system, switching off when a security parameter determined by the internal control unit relating to the wireless energy transfer exceeds a certain threshold.

13. The system of claim 10, wherein said connection between the secondary coil and the medical device is switched on and off in order to enable the system to measure the coupling factor when the connection is off.

14. The system according to claim 1, in which the energy receiver comprises an electronic component connected to the secondary coil for preventing flow of electrical current between the secondary coil and the medical device during measurement of parameters related to the coupling factor.

15. The system according to claim 14, in which the electronic component is a diode.

16. The system according to claim 1, further comprising an electronic component which is connected to the secondary coil for preventing the flow of electrical current between the secondary coil and the medical device during measurement of at least one of the first, second and third parameters such that the secondary coil is substantially without electrical load when measuring the coupling factor.

17. The system according to claim 1, in which the energy receiver comprises a half wave rectifier for rectifying half of the pulse cycle of a received, alternating current energy signal in the energy receiver.

18. The system according to claim 1, in which the external energy source further comprises an electronic circuit for comparing the feedback information with the amount of energy transmitted by the external energy source.

19. The system according to claim 1, further comprising the internal control unit adapted to determine the energy balance between the energy received by the energy receiver and the energy used by the medical device, and the external control unit adapted to calibrate the transmission of wireless energy from the energy source using the feedback information.

20. The system according to claim 1, further comprising at least one energy stabilizing unit in or connected to the medical device, arranged to stabilize received energy prior to use by the medical device.

21. The system of claim 1, wherein the certain amount of time is 50-200 ms.

22. A method for use with a medical system, which comprises internal parts for implantation in a patient and external parts for use externally to the patient, the external parts comprising:
an energy source equipped with a primary coil for inductively transmitting energy to implantable parts,
a control unit for the control of the energy source,
the internal parts comprising:
an electrically powered medical device,
an energy receiver equipped with a secondary coil for inductively receiving energy for the medical device from the external energy source, and
a control unit for the control of the internal parts,
the method comprising the step of determining a balance between the amount of energy received in the energy receiver and the amount of energy used by the medical device, and the step of letting the internal control unit wirelessly transmit feedback information to the external control unit, the method being characterized in that it comprises the step of determining the feedback information based on or relating to a first and a second and a third parameter, and the step of letting the first parameter be based on the energy balance over a certain amount of time and letting the second parameter be based on information relating to a coupling factor between the primary and the secondary coils, and letting the third parameter be based on at least one of the following:
a) further comprising the step of determining a difference between an input voltage to a voltage regulator which is comprised in the medical device in order to keep a voltage constant, and a voltage which the voltage regulator is arranged to keep constant, the method also comprising the step of using the third parameter, said third parameter comprising or being based on said voltage difference, the method also
comprising the step of taking into account the third parameter in order to determine the amount of energy which should transmitted by the external energy source, and
b) further comprising the step of determining a difference between an input current to a current regulator which is comprised in the medical device in order to keep a current constant, and a current which the current regulator is arranged to keep constant, the method also comprising the step of using the third parameter, said third
parameter comprising or being based on said current difference, the method also comprising the step of taking into account the third parameter in order to determine the amount of energy which should transmitted by the external energy source,
the method also comprising the step of using at least both the first and second and third parameters to determine the amount of energy which should be transmitted by the energy source, thus allowing for a rapid adjustment of the energy balance.

* * * * *